US00PP19064P3

(12) United States Plant Patent

Bacon et al.

(10) Patent No.: US PP19,064 P3

(45) Date of Patent: Aug. 5, 2008

(54) PLUM TREE NAMED 'SUPLUMTHIRTYONE'

(50) Latin Name: *Prunus salicina*
Varietal Denomination: Suplumthirtyone

(75) Inventors: Terry A. Bacon, Bakersfield, CA (US); Bruce D. Mowrey, Watsonville, CA (US); David W. Cain, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 231 days.

(21) Appl. No.: 11/329,331

(22) Filed: Jan. 10, 2006

(65) Prior Publication Data

US 2007/0163012 P1 Jul. 12, 2007

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP7,420 P 1/1991 Zaiger et al.

*Primary Examiner*—Annette H Para
(74) *Attorney, Agent, or Firm*—Knobbe, Martens Olson & Bear, LLP

(57) ABSTRACT

A new and distinct plum variety that possesses heavy and consistent production of large (about 65 mm) fruit in late July and early August in Kern County, California. The fruit skin has a smooth yellow finish with mildly-tart flavor, while the flesh color is yellow, with crisp, juicy texture. The flavor is sweet with high sugar levels (about 18° brix), and balancing acidity.

1 Drawing Sheet

Figure 1:
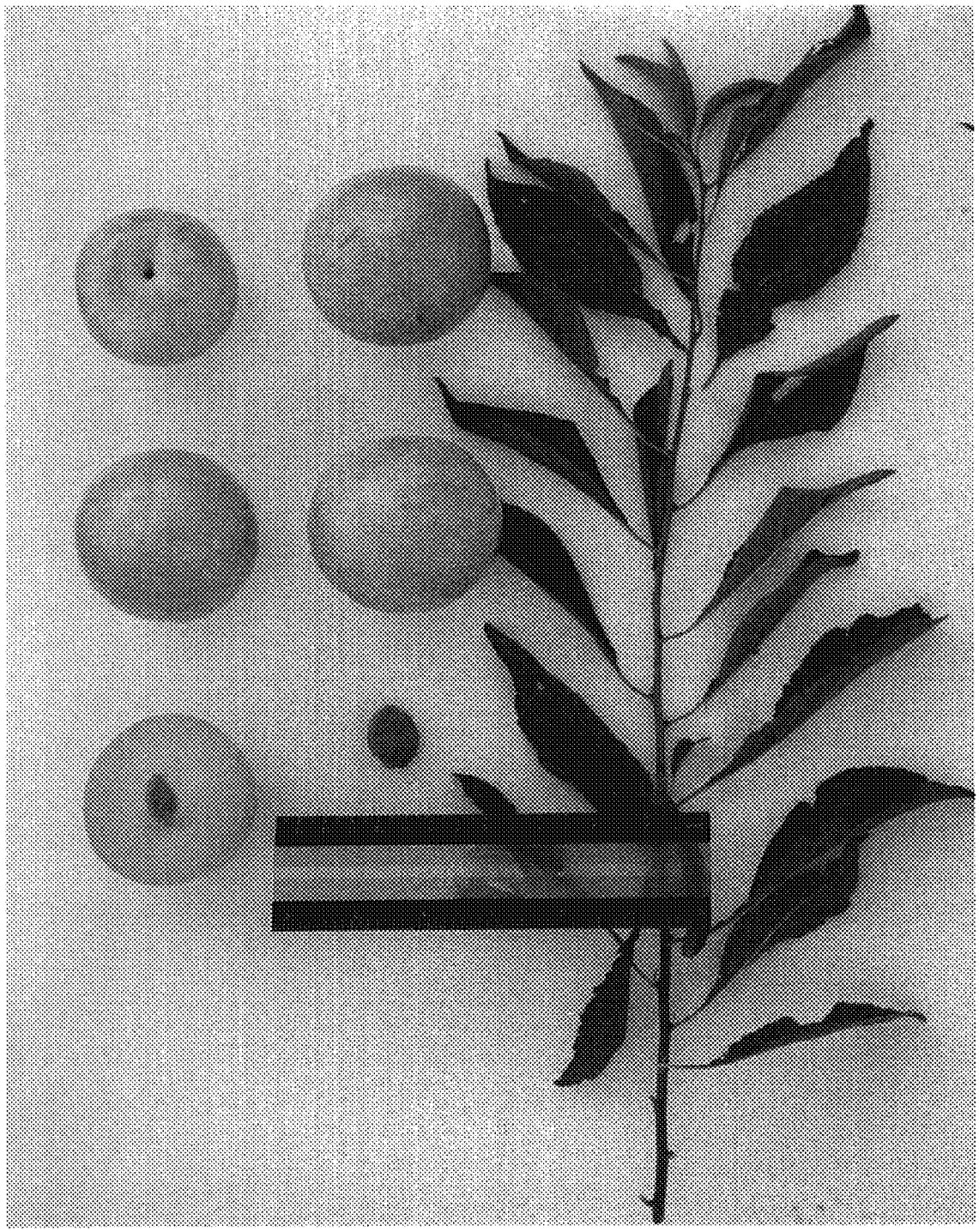

Latin name of the genus and species of the plant claimed: *Prunus salicina.*

Variety denomination: 'Suplumthirtyone'.

BACKGROUND AND SUMMARY OF THE INVENTION

This invention relates to the discovery and asexual propagation of a new and distinct variety of plum, *Prunus salicina* variety 'Suplumthirtyone.' The variety originated by hybridization, being first hybridized by Bruce Mowrey in March 1993, and selected by David Cain as '93P062-119-187.' The new variety was first evaluated during August 1998, by David Cain and Terry Bacon near Wasco, Kern County, Calif.

The new variety 'Suplumthirtyone' is characterized by producing fruit with a yellow-colored flesh with a crisp, juicy texture and a sweet flavor. The variety has a high sugar content (18° brix) and balanced acidity. The fruit skin has a smooth yellow finish with mildly-tart flavor. The new variety 'Suplumthirtyone' has heavy and consistent production of large (65 mm) fruit in late July and early August in Kern County.

The new variety 'Suplumthirtyone' was selected from an open pollinated progeny of the '90P-059' (unpatented), which was selected from a progeny of 'Queen Rosa' (unpatented) crossed with pollen of '232-205' (unpatented). The parent varieties were first crossed in March 1993, with the date of planting of February 1994, and the date of first flowering being 1996. The new plum variety was first asexually propagated by David Cain near Wasco, Kern County, Calif. in 1997, by budding onto 'Nemared' (unpatented) rootstock. The new variety has been shown to maintain its distinguishing characteristics through successive asexual propagations.

The new variety 'Suplumthirtyone' is similar to its seed parent '90P-059' in most characteristics. However, the new variety differs from its seed parent in that the new variety ripens approximately 4 weeks later and has larger fruit (approximately 65 mm diameter compared to approximately 63 mm for '90P-059').

The new variety 'Suplumthirtyone' most nearly resembles the commercial plum 'Flavor Queen' (U.S. Plant Pat. No. 7,420) but may be distinguished from 'Flavor Queen' by the following combination of characteristics: the new variety has larger fruit (approximately 65 mm compared to approximately 63 mm for 'Flavor Queen'), and has yellow skin compared to the greenish-yellow skin of 'Flavor Queen.'

BRIEF DESCRIPTION OF THE PHOTOGRAPH

The accompanying color photographic illustration (FIG. 1) shows typical specimens of the foliage and fruit of the present new plum variety 'Suplumthirtyone.' The illustration shows the upper and lower surface of the leaves, an exterior and sectional view of a fruit divided across its suture plane to show flesh color, pit cavity and the stone remaining in place. The photographic illustration was taken shortly after the fruit was picked (shipping ripe) and the colors are as nearly true as is reasonably possible in a color representation of this type.

DETAILED BOTANICAL DESCRIPTION OF THE INVENTION

The descriptive matter which follows pertains to five year old 'Suplumthirtyone' plants grown in the vicinity of Wasco, Kern County, Calif., during 2002, on 'Nemared' rootstock. The descriptive matter is believed to apply to plants of the variety grown under similar conditions of soil and climate elsewhere.

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

The new variety 'Suplumthirtyone' has not been observed under all possible environmental conditions. The phenotype may vary somewhat with variations in environment such as temperature, daylength, and light intensity, without, however, any variance in genotype.

TREE

General: (Measurements taken on five year old tree unless otherwise noted.).

*Height.*—Medium. Normal for most plum varieties. Reaches a height of approximately 3 meters including normal pruning.

*Spread.*—Varies depending on planting/training system. A typical vase training system planted 5 meters between trees has a tree spread of about 4.3 meters, including pruning.

*Vigor.*—Vigorous; growth of approximately 1.8 to 2 meters height the first growing season.

*Growth.*—Upright-spreading.

*Productivity.*—Productive. Fruit set is usually two or more times desired amount for marketable size fruit. Thinning and spacing of fruit is necessary.

*Form.*—Vase formed.

*Bearer.*—Regular. No alternate bearing observed.

*Fertility.*—Unknown, should be planted with another plum variety to ensure consistent production.

*Canopy density.*—Dense. Pruning is required to open tree vase shape, allowing more sunlight to center of tree.

*Hardiness.*—Hardy in all fruit growing areas of California. Winter chilling requirement is approximately 600 hours at or below 7.2° C.

*Diseases resistance/susceptibility.*—No specific testing for relative plant disease resistance or susceptibility has been designed. Under close observation in Wasco, Kern County, Calif., no particular plant/fruit disease resistance/susceptibility has been observed.

Trunk: (Measurements at 30 cm above soil line.).

*Diameter.*—Approximately 17 cm. Varies with soil type, fertility, climatic conditions and cultural practices.

*Surface texture.*—Medium shaggy, increases with age of tree.

*Color.*—About Greyed-green 197D to about Greyed-green 197B on exposed areas and about Greyed-orange 165B in recesses. Becomes darker with age.

Branches: (Measurements at 90 cm above soil line.).

*Diameter.*—Ranges from approximately 6 to 7 cm.

*Surface texture.*—Smooth on first year wood, increasing roughness with tree age.

*Color.*—About Greyed-green 197D to about Greyed-green 197B on exposed areas and about Greyed-orange 165B in recesses.

*Lenticels.*—Number: Numerous=Approximately 1.5 per square centimeter. Color: About Greyed-orange 165B. Length: Approximately 4 mm. Width: Approximately 2 mm.

Flowering shoots: (Data taken in July at midpoint of current-season growth.).

*Diameter.*—Approximately 5 mm.

*Color.*—Topside: About Greyed-orange 167A with greenish background. Underside: About Green 138B.

*Leaf buds.*—Shape: Ovoid. Length: Approximately 1.5 mm. Width: Approximately 1.2 mm. Color: About Greyed-orange 164A.

*Flower buds.*—Shape: Plump-ovoid. Length: Approximately 1.5 mm. Width: Approximately 1.3 mm. Color: About Greyed-orange 164A. Number per node: Usually 2 to 4.

*Lenticels.*—Absent.

FOLIAGE

Leaves: (Data taken in July on fully expanded leaf at midpoint of current-season growth.).

*Size.*—Average length: Approximately 115 mm. Average width: Approximately 30 mm.

*Thickness.*—Medium.

*Color.*—Upper surface: About Green 136A. Lower surface: About Green 136C.

*Form.*—Elliptic.

*Tip.*—Acuminate.

*Base.*—Acuminate.

*Margin.*—Irregularly crenate.

*Venation.*—Pinnately net veined.

*Vein color.*—About Yellow-green 148B.

*Surface texture.*—Smooth.

*Petiole.*—Average length: Approximately 15 mm. Average diameter: Approximately 2 mm. Color: About Green 138A.

*Stipules.*—Color: About Green 136A. Number per leaf bud: 2. Typical length: Approximately 3 to 5 mm.

*Glands.*—Form: Globose. Number: Varies from 0 to 4. Position: Alternate on upper portion of petiole and base of leaf blade. Average size: Approximately 0.5 mm by 0.5 mm. Color: About Greyed-red 178A.

FLOWERS

General: (Fully opened.).

*Duration of bloom.*—Typically about 10 days from first bloom to petal fall in Central San Joaquin Valley. Varies widely depending on temperatures during bloom and conditions prior to bloom.

*Blooming period.*—First bloom: Feb. 25, 2002. Full bloom: Feb. 28, 2002.

*Diameter of fully opened flower.*—Approximately 20 mm.

*Aroma.*—Very slight.

Peduncle:

*Length.*—Approximately 9 mm.

*Diameter.*—Approximately 0.8 mm.

*Color.*—About Greyed-yellow 160A.

Petals:

*Number.*—5.

*Arrangement.*—Free.

*Length.*—Approximately 10 mm.

*Width.*—Approximately 7 mm.

*Shape.*—Elliptic.

*Apex shape.*—Rounded with slight tip.

*Base shape.*—Narrows at point of attachment.

*Color.*—White 155.

*Surface texture.*—Smooth.

*Margins.*—Undulating.

Sepals:

*Number.*—5.

*Length.*—Approximately 4.5 mm.

*Width.*—Approximately 3 mm.
*Shape.*—Elliptic with slight point.
*Color.*—About Yellow-green 145A.
*Surface texture.*—Smooth.

Stamens:
*Number.*—Approximately 22 to 30, average 28.
*Average length.*—Approximately 8 mm.
*Filament color.*—White 155.
*Anther color (just prior to dehiscence).*—About Yellow-orange 20B.
*Pollen color.*—About Yellow-orange 20B.

Pistil:
*Number.*—Usually one, occasionally two, many flowers have pistils that are stunted or undeveloped.
*Average length.*—Approximately 7 mm.
*Ovary diameter.*—Approximately 2 mm.
*Pubescence.*—None.
*Stigma extension.*—Stigma extends below anthers.

FRUIT

General: (Data taken at firm-ripe stage on mature tree managed to obtain maximum quality under conditions stated above.).
*Harvest.*—Date of first pick: Jul. 22, 2002. Date of last pick: Aug. 5, 2002.

Size: (Under conditions typical of the San Joaquin Valley, Calif.).
*Length (stem end to apex).*—Approximately 66 mm.
*Diameter in line with suture plane.*—Approximately 65 mm.
*Diameter perpendicular to suture plane.*—Approximately 65 mm.
*Average weight.*—Approximately 153 gm.

Form:
*Viewed from apex.*—Rounded, summetrical.
*Viewed from side, facing suture.*—Rounded to elongated, with extended apex on many fruit.
*Viewed from side, perpendicular to suture.*—Rounded to elongated, with extended apex on many fruit.

Apex shape: Extended apex on many fruit.

Stem-end cavity depth: Shallow.

Stem:
*Length.*—Approximately 9 mm.
*Diameter.*—Approximately 2 mm.
*Color.*—About Green 143C.

Skin:
*Thickness.*—Medium.
*Adherence to flesh.*—Tenacious.
*Surface texture.*—Smooth.
*Pubescence.*—None.
*Bloom.*—Moderate amount.
*Ground color.*—About Yellow-green 150C when present.
*Overcolor.*—About Yellow-orange 21C.
*Taste.*—Mildly tart.

Flesh:
*Ripens.*—Evenly.
*Texture.*—Fine, firm, very juicy.
*Fibers.*—Few.
*Flavor.*—Sweet-tart, becoming mildly-sweet as fruit ripens.
*Brix.*—Approximately 18 degrees.
*Juice.*—Plentiful.
*Aroma.*—Moderate.
*Color.*—About Yellow-orange 16C, uniform.
*Pit cavity.*—Pit cavity size: Approximately 22 mm; diameter in line with suture plane: approximately 18 mm; diameter perpendicular to suture plane: approximately 8 mm. Pit cavity color: About Yellow-orange 16C.
*Fruit use.*—Dessert. Market, local and long distance.
*Fruit shipping/keeping quality.*—Good. Holds well in cold storage for approximately 6 weeks and maintains good firmness and eating quality. Minimal bruising and scarring in packing and shipping trials.

Stone: (Measurements taken on dried stones.).
*Freeness.*—Clingstone.
*Size.*—Length: Approximately 22 mm. Diameter in line with suture plane: Approximately 18 mm. Diameter perpendicular to suture plane: Approximately 8 mm.
*Form (viewed from side).*—Rounded, slightly asymmetrical.
*Form (viewed from stem end).*—Oval, flattened, symmetrical.
*Base shape.*—Flattened, retuse at stem attachment.
*Apex shape.*—Rounded with a small, dull point.
*Surface.*—Irregularly furrowed near base. Lightly ridged toward base. Lightly pitted throughout.
*Halves.*—Equal.
*Ridges.*—1 on each side of the suture. The ridges are small and narrow beginning at the base and extending throughout the length of the stone.
*Outgrowing keel.*—Well developed.
*Tendency to split.*—None.
*Color.*—About Greyed-orange 164C when dried.

What is claimed is:

1. A new and distinct plum tree as herein described and illustrated.

* * * * *